US00PP28848P2

(12) United States Plant Patent
Smit

(10) Patent No.: US PP28,848 P2
(45) Date of Patent: Jan. 2, 2018

(54) *CALLISIA* PLANT NAMED 'ROSATO'

(50) Latin Name: *Callisia repens*
Varietal Denomination: Rosato

(71) Applicant: Obed Jacob Smit, Sappemeer (NL)

(72) Inventor: Obed Jacob Smit, Sappemeer (NL)

(73) Assignee: Eden CollecTion B.V., Sappemeer (NL)

( * ) Notice: Subject to any disclaimer, the term of this patent is extended or adjusted under 35 U.S.C. 154(b) by 0 days.

(21) Appl. No.: 15/330,480

(22) Filed: Sep. 26, 2016

(51) Int. Cl.
*A01H 5/12* (2006.01)

(52) U.S. Cl.
USPC ..... Plt./373

(58) Field of Classification Search
USPC ..... Plt./373
See application file for complete search history.

(56) References Cited

PUBLICATIONS

Pluto Plant Variety database Aug. 30, 2017. p. 1.*

* cited by examiner

*Primary Examiner* — Annette H Para

(57) ABSTRACT

A new cultivar of *Callisia* plant named 'Rosato' that is characterized by bi-colored pink-green leaves and a compact habit.

1 Drawing Sheet

Botanical classification: *Callisia repens.*
Variety denomination: 'Rosato'.

BACKGROUND OF THE INVENTION

The present invention relates to a new and distinct cultivar of *Callisia* plant botanically known as *Callisia repens* and hereinafter referred to by the cultivar name 'Rosato'.

'Rosato' was discovered as a naturally occurring branch mutation of *Callisia repens* 'Turtle' (not patented). 'Rosato' was discovered by the inventor in 2013 in a greenhouse in a cultivated area of Sappemeer, Netherlands.

Asexual reproduction of the new cultivar 'Rosato' first occurred by tip cuttings in 2014 in Sappemeer, Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Callisia* cultivar 'Rosato'. These traits in combination distinguish 'Rosato' as a new and distinct cultivar apart from other existing varieties of *Callisia* known by the inventor.

1. *Callisia* 'Rosato' exhibits bi-colored pink-green leaves.
2. *Callisia* 'Rosato' exhibits a compact habit.

The closest comparison cultivars are *Callisia* 'Yellow Turtle' (not patented) and *Callisia* 'Bianca' (not patented). 'Rosato' is distinguishable from 'Yellow Turtle' by the following characteristics:

1. *Callisia* 'Rosato' exhibits bi-colored pink-green leaves. In comparison, the leaves of 'Yellow Turtle' are yellow-green.

'Rosato' is distinguishable from 'Bianca' by the following characteristics:

1. *Callisia* 'Rosato' exhibits bi-colored pink-green leaves. In comparison, 'Bianca' has a mixture of individual leaves that are green, pink-green and striped.
2. *Callisia* 'Rosato' exhibits smaller leaves than the leaves of 'Bianca'.

'Rosato' is distinguishable from the parent plant, by the following characteristics:

1. *Callisia* 'Rosato' exhibits bi-colored pink-green leaves. In comparison, the leaves of the parent plant are green.

BRIEF DESCRIPTION OF THE DRAWING

The accompanying photograph illustrates the distinguishing traits of *Callisia* 'Rosato'. The photograph shows an overall view of a 12 week old plant. The photograph was taken using conventional techniques and although colors may appear different from actual colors due to light reflectance, it is as accurate as possible by conventional photographic techniques.

BOTANICAL DESCRIPTION OF THE PLANT

The following is a detailed description of the new *Callisia* cultivar named 'Rosato'. Data was collected in Sappemeer, Netherlands from 12 week old plants grown in a glass greenhouse in 10.5 cm. diameter containers. The time of year was Winter and the temperature range was 18-25 degrees Centigrade during the day and 15-18 degrees Centigrade at night. The light level was natural light level. No photoperiodic treatments or growth retardants were used. Color determinations are in accordance with The Royal Horticultural Society Colour Chart 2015 edition, except where general color terms of ordinary dictionary significance are used. The growing requirements are similar to the species. 'Rosato' has not been tested under all possible conditions and phenotypic differences may be observed with variations in environmental, climatic, and cultural conditions, however, without any variance in genotype.

Botanical classification: *Callisia repens* 'Rosato'.
Annual or perennial: Perennial.
Parentage: 'Rosato' was discovered as a naturally occurring branch mutation of *Callisia repens* 'Turtle'.
Plant type: Potted plant.
Growth habit: Broad spreading upright.
Plant shape: Flattened globe shaped.
Suitable container size: 7 cm. pots or larger.
Plant height: 7.0 cm.
Plant width: 17.3 cm.
Vigor: Low to moderate.
Low temperature tolerance: 10° Centigrade.
High temperature tolerance: 35° Centigrade.
Propagation: Tip cuttings.
Time to initiate roots (summer): 7 days at 18 to 20° C.
Time to initiate roots (winter): 14 days at 18 to 20° C.
Time to produce a rooted cutting: Cuttings are placed directly into growing pots.
Growth rate: Low to moderate.
Crop time: Approximately 10 to 12 weeks in Sappemeer, Netherlands.
Root system: Fine and fibrous.
Plant fragrance: None.
Stem:
*Branching habit*.—Main and lateral branches.
*Number of main branches per plant*.—Average 40.
*Number of lateral branches per plant*.—Average 170.
*Lateral branch dimensions*.—4.9 cm. in length and 0.15 cm. in diameter.
*Internode length*.—0.4 cm.
*Stem shape*.—Rounded.
*Stem luster*.—Slightly glossy.
*Stem pubescence*.—Covered with short soft hairs.
*Stem angle*.—Average 45 degrees.
*Stem strength*.—Moderately strong.
*Stem color* (*young*).—143B.
*Stem color* (*mature*).—72B and NN74B.
*Internode color*.—72B.
Foliage:
*Leaf arrangement*.—Distichous.
*Compound or single*.—Single.
*Leaf attachment*.—Sessile.
*Quantity of leaves per lateral branch*.—Average 13.
*Leaf shape*.—Ovate to elliptic.
*Leaf aspect*.—Flat to slightly carinate.
*Leaf apex*.—Acute.
*Leaf base*.—Cuneate, sheathing.
*Sheath dimensions*.—0.3 cm. in length and 0.2 cm. in width.
*Sheath color*.—NN155D with stripes 71A.
*Leaf dimensions*.—1.2 cm. in length and 0.65 cm. in width.
*Texture*.—Smooth (both surfaces).
*Leaf luster*.—Upper surface moderately glossy, lower surface slightly glossy.
*Pubescence* (*both surfaces*).—Base of leaf covered with short soft hairs, 0.15 cm. in length, NN155D in color.
*Leaf rugose*.—Not rugose.
*Leaf margin*.—Entire.
*Venation pattern*.—None.
*Young leaf color* (*upper surface*).—62D and 63D with irregular stripes 146B and 146C and fine dots 71A.
*Young leaf color* (*lower surface*).—70B with irregular stripes 147B.
*Mature leaf color* (*upper surface*).—145D, 62C and N75B with irregular stripes 143A, 143B, 144A, 144B, 146A, 147A and fine dots 71A.
*Mature leaf color* (*lower surface*).—70B with irregular stripes 147B.
Flower: 'Rosato' has not produced flowers to date.
Fruit and seed: 'Rosato' has not produced fruit or seed to date.
Disease and pest resistance: Disease and pest resistance has not been observed.

The invention claimed is:

1. A new and distinct variety of *Callisia* plant named 'Rosato' as described and illustrated.

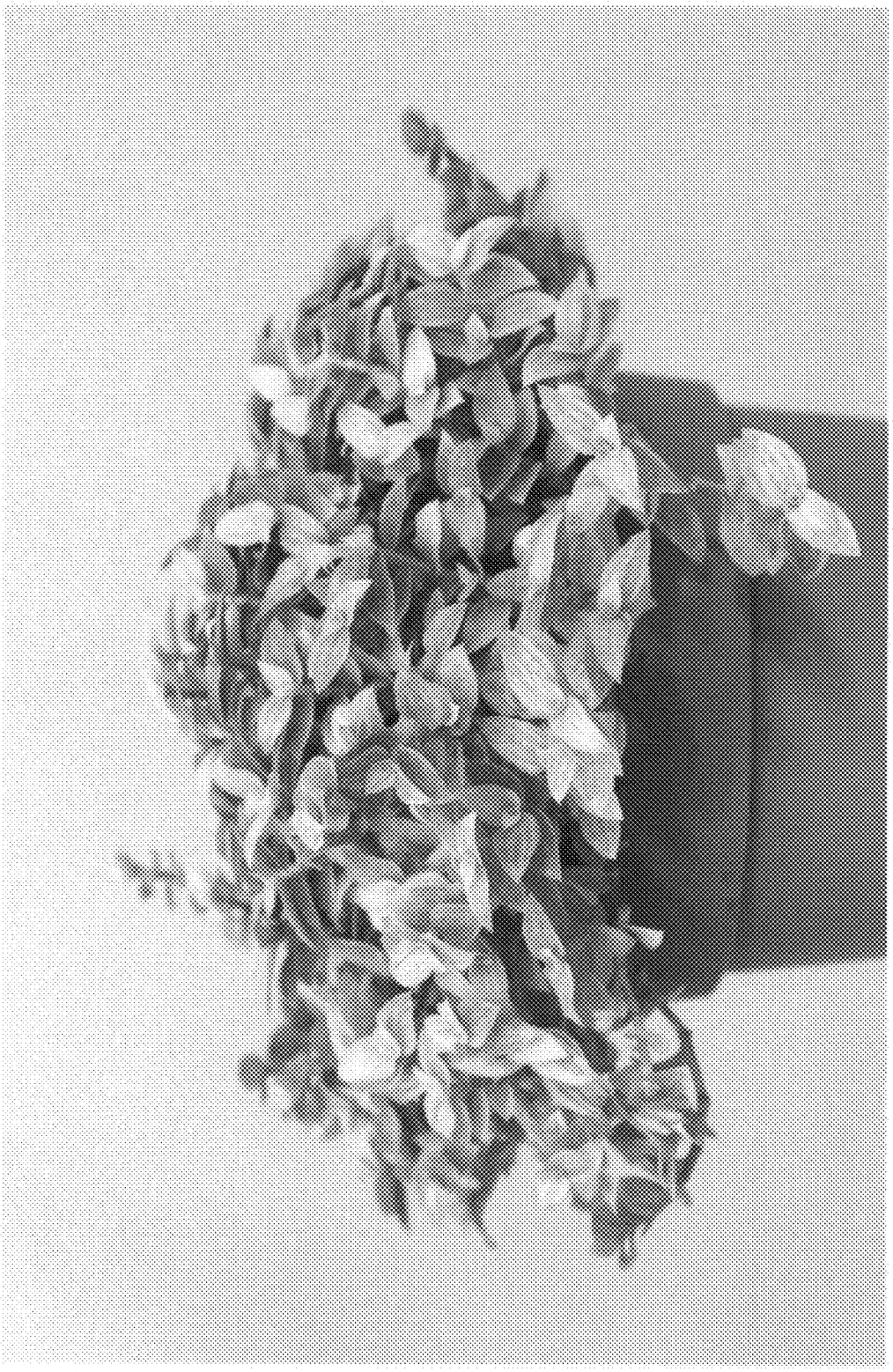

* * * * *